United States Patent [19]

Chu et al.

[11] Patent Number: 4,513,092
[45] Date of Patent: Apr. 23, 1985

[54] COMPOSITE CATALYST FOR HALOGENATION AND CONDENSATION OF ALKANES

[75] Inventors: Pochen Chu, Deptford, N.J.; Francis G. Dwyer, West Chester, Pa.

[73] Assignee: Mobil Oil Corporation, New York, N.Y.

[21] Appl. No.: 594,583

[22] Filed: Mar. 29, 1984

Related U.S. Application Data

[63] Continuation-in-part of Ser. No. 568,153, Jan. 4, 1984.

[51] Int. Cl.³ .............................................. B01J 29/30
[52] U.S. Cl. ...................................... 502/71; 502/60; 502/77
[58] Field of Search ....................... 502/65, 73, 60, 69, 502/71; 585/310

[56] References Cited

U.S. PATENT DOCUMENTS

| | | | |
|---|---|---|---|
| 3,184,515 | 5/1965 | Penner et al. | 260/658 |
| 3,314,760 | 4/1967 | Trapasso | 23/204 |
| 3,546,306 | 12/1970 | McCarthy | 502/60 X |
| 3,634,330 | 1/1972 | Michel et al. | 252/441 |
| 4,096,163 | 6/1978 | Chang et al. | 260/449 R |
| 4,323,716 | 4/1982 | Canavesi et al. | 570/243 |

*Primary Examiner*—Carl F. Dees
*Attorney, Agent, or Firm*—A. J. McKillop; M. G. Gilman; L. G. Wise

[57] ABSTRACT

A dual-function chlorination-condensation catalyst composition consisting essentially of (a) Deacon-type catalyst comprising cupric halide, alkaline earth halide and/or alkali metal halide, and/or rare earth metal halide and (b) crystalline aluminosilicate zeolite catalyst, such as ZSM-5 type.

8 Claims, No Drawings

COMPOSITE CATALYST FOR HALOGENATION AND CONDENSATION OF ALKANES

REFERENCE TO COPENDING APPLICATION

This application is a continuation-in-part of U.S. patent application Ser. No. 568,153 filed Jan. 4, 1984, incorporated herein by reference.

FIELD OF INVENTION

This invention relates to a composite catalyst for converting natural gas or other alkane feedstock to higher hydrocarbons, such as gasoline, blending stocks or petrochemical materials. In particular, it relates to novel catalyst compositions.

BACKGROUND OF THE INVENTION

The relative abundance of methane in natural gas and high cost of petroleum raw materials has led workers in the field of fossil fuel technology to seek economic processes for conversion of lower alkanes to higher hydrocarbons in the gasoline and diesel range for use as liquid fuels. The $C_5^{30}$ aliphatic and aromatic hydrocarbons are particularly useful as spark-ignited fuel for internal combustion engines. Steam reforming of methane-rich feedstocks to produce CO and $H_2$ syngas can be followed by conventional methanol synthesis or Fischer-Tropsch reactions to provide oxygenated feedstock suitable for hydrocarbon conversion over a particular class of crystalline medium pore zeolites, known as ZSM-5 catalysts.

A substantial effort has been made in developing a methanol-to-gasoline ("MTG") process, as described in U.S. Pat. Nos. 3,894,107 (Butter et al), 4,013,731 (Chang et al), 4,118,431 (Chen), 4,251,484 (Daviduk et al). Other disclosures involving ZSM-5 type catalysts for converting synthesis gas to gasoline-range hydrocarbons are U.S. Pat. 4,159,995 (Haag et al), 4,093,029 (Weisz et al).

SUMMARY OF THE INVENTION

A dual function composite catalyst has been discovered comprising an intimate mixture of a Deacon-type catalyst and a medium pore acid zeolite catalyst. This novel catalyst can be employed in an integrated process for halogenating alkanes and condensing the haloalkane intermediate to produce higher hydrocarbons. In a preferred embodiument, the dual-function catalyst consists essentially of a Deacon-type catalyst deposited on alumina and composited with HZSM-5 crystals. Typical Deacon-type catalysts include $CuCl_2$, alkali metal or alkaline earth chloride, and rare earth chloride impregnated on a solid carrier.

DESCRIPTIION OF PREFERRED EMBODIMENTS

Halohydrocarbons can be made from lower aliphatic compounds by a number of halogenation processes. Primary emphasis in this description is placed on chlorination of methane and other components of natural gas as a preferred economic process for making higher hydrocarbons. $C_1$ to $C_3$ paraffins are abundant in nature, frequently occuring with carbon dioxide and trace amounts of $C_4+$ hydrocarbons. A typical dry gas feedstock may contain $90+$ vol. % $CH_4$ and lesser amounts of $CO_2$, ethane, etc.

A suitable halogenation gas may include molecular chlorine ($Cl_2$) or hydrogen chloride (HCL) with oxygen. It is well known that halogen gases may be generated by heating hydrogen halide in contact with an oxygen-containing gas, such as air. When combined with heated methane over a Deacon-type catalyst, a typical halogenation reaction occurs as follows:

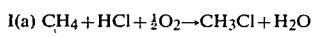

$$I(a) \; CH_4 + HCl + \tfrac{1}{2}O_2 \rightarrow CH_3Cl + H_2O$$

Deacon catalysts are well-known materials and are commonly used in halogenation reactions, especially where HCl is oxidized as part of the reaction. Although catalyst melts are known, particulate catalysts such as obtained by impregnating cupric halide on calcined alumina are preferred, especially those Deacon catalysts which consist essentially of cupric chloride, alkali metal chloride and rare earth chloride calcined on alumina. Preparation of suitable catalysts is described in U.S. Pat. Nos. 3,184,515; 3,634,330 and 4,323,716. Halogenation processes are disclosed in U.S. Pat. Nos. 2,957,924; 3,314,760; 1,654,821 and 4,199,533.

In U.S. Pat. No. 2,488,083 (Gorin et al), incorporated herein by reference, such an oxyhalogenation first stage reaction is combined with a catalytic second stage condensation reaction to produce higher hydrocarbons, including $C_2$–$C_4$ paraffins and olefins and $C_5+$ aliphatics and aromatics. The Gorin catalysts included alumina, silica and related condensation catalysts. The second stage dehydrohalogenation reaction may be simplified as follows:

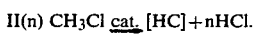

$$II(n) \; CH_3Cl \xrightarrow{cat.} [HC] + nHCl.$$

It is recognized that the hydrocarbon products (HC) may include light gases, such as ethane, propane, propylene, butanes, etc., as well as the condensed liquid hydrocarbon product and halogenated by-product.

A process for converting aliphatic halides using ZSM-5 type zeolite catalysts is described by Butter et al in U.S. Pat. No. 3,894,107, incorporated herein by reference. The preferred catlysts are crystalline aluminosilicates having a high silica to alumina ratio of at least about 12 and a constraint index of about 1 to 12. In the acid form these are often denominated HZSM-5 type materials. Co-extruded with alumina, these active catalysts are available in various forms and sizes such as 1/16" cylindrical extrudate particles.

The members of the class of medium pore crystalline zeolites for use in this invention are characterized by a pore dimension greater than about 5 Angstroms, i.e., it is capable of sorbing paraffins having a single methyl branch as well as normal paraffins, and it has a silica to alumina mole ratio of at least 12. Zeolite A, for example, with a silica to alumina ratio of 2.0, is not useful in this invention, and moreover it has no pore dimension greater than about 5 Angstroms.

The members of the class of crystalline zeolites for use herein constitute an unusual class of natural and synthetic minerals. They are characterized by having a rigid crystalline framework structure composed of an assembly of silicon and aluminum stoms, each surrounded by a tetrahedron of shared oxygen atoms, and a precisely defined pore structure. Exchangeable cations are present in the pores.

These zeolites induce transformations of substituted and unsubstituted aliphatic hydrocarbons to higher aliphatic or aromatic hydrocarbons in commercially desirable yields and generally highly effective in condensing halohydrocarbons. Although they have unusually low alumina contents, i.e., high silica to alumina mole ratios, they are very active even with silica to alumina mole ratios exceeding 30. This activity is surprising, since catalytic activity of zeolites is generally attributed to framework alminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at high temperatures, for example, 500° C., to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intracrystalline free space by virtue of having a pore dimension greater than about 5 Angstroms and pore windows of about a size such as would be provided by 10-membered rings of atoms. Since these rings are known to contain the silicon atoms alternating with oxygen, the crystalline materials are sometimes known as pentasils. It is to be understood, of course, that these rings are those formed by the regular disposition of the tetrahedra making up the anionic framework of the crystalline zeolite, the oxygen atoms themselves being bonded to the silicon or aluminum atoms at the centers of the tetrahedra. Briefly, the preferred zeolites useful herein possess, in combination: a Constraint Index, as hereinafter defined, of about 1 to 12, a silica to alumina mole ratio of at least about 12, and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels.

Although such crystalline zeolites with a silica to alumina mole ratio of at least about 12 are useful, it is preferred to use zeolites having higher ratios of at least about 30. In some zeolites, the upper limit of silica to alumina mole ratio is unbounded, with values of 30,000 and greater, extending at least theoretically up to infinity. Therefore, the silica to alumina mole ratio of the zeolite for use herein may be from about 12 to infinity, preferably from about 30 to infinity. Such zeolites, after activation, acquire an intracrystalline sorption capacity for normal hexane which is greater than that for water, i.e., they exhibit "hydrophobic" properties. It is believed tht this hydrophobic character is advantageous in the present invention.

The crystalline zeolites for use in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, the access by molecules of larger cross-section than normal hexane is substantially excluded and the zeolite is not of the desired type. Zeolites with windows of 10-member rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constraint access, a simple determination of the "Constraint Index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluennt is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those which have a Constraint Index from 1 to 12. Constraint Index (C.I.) values for some typical materials are:

| Zeolite | C.I. |
| --- | --- |
| REY | 0.4 |
| H-Zeolon (mordenite) | 0.4 |
| ZSM-4 | 0.5 |
| Acid Mordenite | 0.5 |
| Beta | 0.6–1.6 |
| Amorphous Silica-Alumina | 0.6 |
| ZSM-12 | 2 |
| ZSM-38 | 2 |
| ZSM-48 | 3.4 |
| Clinoptilolite | 3.4 |
| TMA Offretite | 3.7 |
| ZSM-35 | 4.5 |
| ZSM-5 | 8.3 |
| ZSM-11 | 8.7 |
| ZSM-23 | 9.1 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above-defined range of 1 to 12.

Thus, it should be understood that the parameter and property "Constraint Index" as such value is used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The members of the class of zeolites for use herein are exemplified by shape selective medium pore siliceous catalysts, such as ZSM-5, ZSM-5/ZSM-11 intermediate, ZSM-11, ZSM-12, ZSM-22, ZSM-23, ZSM-35, ZSM-38, ZSM-48 and other similar materials. U.S. Pat. No. 3,702,886 describing and claiming ZSM-5 is incorporated herein by reference. Also, U.S. Pat. No. Re. 29,948 describing and claiming a crystalline material with an X-ray diffraction pattern of ZSM-5, is incorporated herein by reference as is U.S. Pat. No. 4,061,724 describing a high silica ZSM-5 referred to as "silicalite" in such patent.

The ZSM-5/ZSM-11 intermediate is described in U.S. Pat. No. 4,229,424. ZSM-11 is described in U.S. Pat. NO. 3,709,979. ZSM-12 is described in U.S. Pat. No. 3,832,449. ZSM-23 is described in U.S. Pat. No. 4,076,842. ZSM-35 is described in U.S. Pat. No. 4,016,245. ZSM-38 is described in U.S. Pat. No. 4,046,859. ZSM-48 is more particularly described in U.S. patent application Ser, No. 303,276, filed Sept. 17, 1981. ZSM-22 is described in pending U.S. patent application Ser. No. 373,451, filed Apr. 30, 1982. The entire contents of the above identified patents are incorporated herein by reference.

The zeolites used in additive catalysts in this invention may be in the hydrogen form or they may be base exchanged or impregnated to contain a metal cation. It is desirable to calcine the zeolite after base exchange.

In a preferred aspect of this invention, the crystalline zeolites are selected as those having a crystal framework density, in the dry hydrogen form, of not substantially below about 1.6 grams per cubic centimeter. It has been found that zeolites which satisfy all three of these criteria are most desired. Therefore, the preferred crystalline zeolite for use in this invention are those having a Constraint Index as defined above of about 1 to 12, a silica to alumina mole ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on *Zeolite Structure* by W. M. Meier. This paper is included in *Proceedings of the Conference on Molecular Sieves,* London, April 1967, published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that the unusual sustained activity and stability of this class of zeolites are associated with its high crystal anionic framework density of not less than about 1.6 grams per cubic centimeter. This high density, of course, must be associated with a relatively small amount of free space within the crystal, which might be expected to result in more stable structures. This free space, however, seems to be important as the locus of catalytic activity.

Crystal framework densities of some typical zeolites, including some which are not within the purview of this invention, are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The catalyst and separate additive composition for use in this invention may be prepared in various ways. They may be separately prepared in the form of particles such as pellets or extrudates, for example, and intimately mixed in the required proportions. The particle size of the individual component particles may be quite samll, for example from about 20 to about 150 microns, when intended for use in fluid bed operation, or they may be as large as up to about ½ inch for fixed bed operation. Or the components may be mixed as powders and formed into composite pellets or extrudate, each pellet containing both components in substantially the required proportions.

It is desirable to incorporate the zeolite component of the separate additive composition in a matrix. Such matrix is useful as a binder and imparts greater resistance to the catalyst for the severe temperature, pressure and velocity conditions encountered in many hydrocarbon conversion processes. Hydrated alumina ($\alpha$-$Al_2O_3 \cdot H_2O$) is a preferred zeolite binder. Other matrix materials include both synthetic and natural substances. Such substances include clays, silica and/or metal oxides. The latter may be either naturally occurring or in the form of gelatinous precipitates, sols or gels including mixtures of silica and metal oxides. Frequently, zeolite materials have been incorporated into naturally occurring clays, e.g. bentonite and kaolin. In addition to the foregoing materials, the zeolite for use herein can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of clay in combination with silica or any of the above specified cogels may be used to form a matrix.

In general, the crystalline zeolites of the catalyst and separate additive composition for use herein are ordinarily ion exchanged either separately or, in the case of additive composition, in the final preparation of such additive composition, with a desired cation to replace alkali metal present in the zeolite as found naturally or as synthetically prepared. The exchange treatment is such as to reduce the alkali metal content to less than about 50% by weight of the original alkali metal contained in the zeolite as synthesized, usually 0.5 weight percent or less. The purpose of ion exchange is to substantially remove alkali metal cations which are known to be deleterious to cracking, as well as to introduce particularly desired catalytic activity by means of the various cations used in the exchange medium. For the hydrocarbon conversion operation described herein, preferred cations are hydrogen, ammonium, rare earth and mixtures thereof, with particular preference being accorded rare earth. Ion exchange is suitably accomplished by conventional contact of the zeolite with a suitable salt solution of the desired cation such as, for example, the sulfate, chloride or nitrate.

The ZSM-5 type catalyst is particularly advantageous in the present integrated process by reason of its hydrophobic nature and resistance to halogen acid deterioration. These characteristics are not readily found in prior art condensation catalysts. By eliminating interstage separation of corrosive inorganic haolgen materials and water from the haloalkanes, an economic process is achieved.

In general, conversion of alkyl halides to useful hydrocarbon product takes place in the temperature range of about 300° C. to 500° C. with or without the presence of hydrogen. Pressures from below atmospheric to about 7000 kPa, are operable, with about 5 to 500 kPa being preferred. Typically, a weight hourly space velocity of about 0.5 to 50 WHSV based on zeolite catalyst content is employed in the catalyst bed.

The various products may be recovered or recycled according to process needs. Unconverted methane and other light gases may be separated and recycled to the catalyst zone. Inorganic halogen-containing gases may be separated for recycle, regeneration or disposal, according to their composition. Halohydrocarbons may be recovered as product or recycled.

EXAMPLE 1

A Deacon-type chlorination catalyst is prepared by impregnating 30 parts of a low surface (14 m²/g) and medium porosity (0.25 ml/g) alumina with a solution of 6.1 parts of $CuCl_2$ $2H_2O$ and 4.2 parts of KCl and 6.4 parts of $RECl_3$ in 60 parts of water. The impregnated extrudates are dried at 110° C., then calcined at 371° C. for 3 hours. An acid ZSM-5 was prepared by calcining the "as synthesized" ZSM-5 ($SiO_2/Al_2O_3=40$) at 538° C. in $N_2$ for 3 hours. The calcined sample is ion exchanged with $NH_4NO_3$ solution to reduce Na to less than 0.02% by weight. The sample is converted into acid form by air calcination at 538° c. for 3 hours. One part of chlorination catalyst and four parts of acid ZSM-5 are composited together.

EXAMPLES 2A–2C

Feedstock of methane and chlorine was reacted over the composite catalyst downflow in a tubular reactor. The operating conditions and results are shown in the table.

TABLE I

Catalyst: Chlorination and ZSM-5 Catalyst Composite
Total Weight: 5 Grams

| Run No. | 2A | 2B | 2C |
|---|---|---|---|
| Feedstock | | | |
| Methane, ml/min | 23.5 | 23.5 | 23.5 |
| Chlorine, ml/min | 5.0 | 5.0 | 5.0 |
| Operating Conditions | | | |
| Temperature, °C. | 427 | 427 | 454 |
| Pressure, psig | 0 | 0 | 0 |
| Time on Stream, hours | 1.5 | 3.0 | 1.0 |
| $CH_4$ Conversion, mol % | 6.09 | 7.3 | 5.08 |
| Product Distribution, mol % | | | |
| $C_1$ | 93.91 | 92.70 | 94.92 |
| $C_2$ | 0.46 | 1.14 | 1.48 |
| $C_3$ | 4.83 | 3.89 | 1.83 |
| $C_4^+$ | 0.82 | 2.26 | 1.77 |

EXAMPLE 3

A chlorination catalyst is prepared by impregnating 100 parts by weight of calcined alumina (Alcoa A-3) with 6.1 parts of $CuCl_2$ $2H_2O$, 2.7 parts of $MgCl_2$ and 6.2 parts of rare earth chloride in 61 parts of water. The impregnated particles are dried at about 100° C. to remove water and calcined at about 370° C. for 3 hours.

The standard acid ZSM-5 catalyst used is the same acid ZSM-5 catalyst described in Example 1 and the same proportions may be employed.

EXAMPLE 4

A Deacon-type oxychlorination catalyst is prepared by impregnating 100 parts by weight of calcined alumina ("Alcoa A-3") with 10.1 parts $CuCl_2$ $2H_2O$, 7.0 parts KCl, and 10.6 parts rare earth chloride dissolved in 100 parts by weight of water. The impregnated particles are dried at about 110° C. to remove water and calcined at about 370° C. for three hours. The Deacon catalyst is mixed with a standard commercially available acid ZSM-5 catalyst containing 65 wt. % ZSM-5 with 35% alumina in 1/16 inch extrudate form. The composite catalyst is four parts of ZSM-5 extrudate and one part of Deacon catalyst.

The Deacon catalyst components may be deposited on a zeolite condensation catalyst as carrier. Typically, the active halogenation components comprise about 1 to 20 weight percent of the active zeolite, with about 3 to 12 wt % being preferred. Typically, a fixed bed catalyst comprises about 10 to 90% active catalytic components, the remainder being inert binder. One skilled in the art will be able to optimize the catalyst structure and composition for a particular halogenation-condensation reaction scheme, depending upon feedstock and process conditions.

In the oxyhalogenation of alkanes, it is advantageous to control the relative amounts of reactant gases to minimize formation of polyhalogenated alkanes, such as methylene chloride ($CH_2Cl_2$), chloroform, dihalo ethanes, etc. This may be achieved in a continuous process by regulating the flow of hydrocarbon gas to maintain a stoichiometric excess relative to the halogen. Ordinarily, the mole ratio of alkane to halogen is in the range of about 1:1 to 10:1. To avoid deleterious effects in the system, it may be desirable to limit halogen-acid gas concentration, especially where gases such as HCl or HBr could combine with water.

Direct halogenation of lower alkanes is a well-known industrial process. In the absence of light or catalyst, thermal chlorination of methane is carried out as a chain reaction by thermal dissociation of $Cl_2$. A lower activation energy is required for catalytic chlorination. Direct chlorination may be depicted by the following:

III. $CH_4 + Cl_2 \rightarrow CH_3Cl + HCl$.

Both direct chlorination and oxychlorination are believed to proceed by generating chlorine atoms, which react with methane to form HCl and a methyl radical. The $CH_3\cdot$ radical in turn reacts with chlorine to form mono-chloromethane.

The addition of oxygen to halogenation gases is well known. Hydrohalogens (HX) are converted to halogen and water by heating with an oxygen-containing gas such as air or pure $O_2$. Where oxygen is maintained in stoichiometric excess to HX, little if any halogen acid gas will escape the halogenation zone. For this reason, oxyhalogenation is advantageous as compared to direct halogenation. Where $O_2 Cl_2$ are present in the halogenation gas, HCl formed in reaction I(b) is reacted with alkane and $O_2$ for further conversion according to reaction I.

What is claimed is:

1. A dual-function chlorination-condensation catalyst composition consisting essentially of (a) Deacon-type catalyst comprising cupric halide, alkaline earth halide and/or alkali metal halide, and/or rare earth metal halide and (b) crystalline aluminosilicate zeolite component having a silica to alumina ratio of at least 12 and constraint index of 1 to 12.

2. The catalyst composition of claim 1 wherein the Deacon-type catalyst comprises about 1 to 20 weight percent of the zeolite component.

3. The catalyst composition of claim 2 wherein the dual function catalyst contains 10 to 90 weight percent alumina binder.

4. The catalyst composition of claim 2 wherein the zeolite consists essentially of acidic ZSM-5, having a silica:alumina mole ratio greater than 30:1.

5. The dual-function catalyst of claim 4 wherein the Deacon-type catalyst is deposited on alumina and composited with HZSM-5 crystals.

6. The catalyst composition of claim 1 wherein the Deacon-type catalyst include $CuCl_2$, alkali metal or alkaline earth chloride, and rare earth chloride impregnated on alumina.

7. A dual function composite catalyst comprising an intimate mixture of a Deacon-type catalyst and a medium pore acid ZSM-5 type zeolite catalyst.

8. The component catalyst of claim 7 wherein the zeolite comprises a crystalline aluminosilicate having a silica:alumina mole ratio of at least 30:1 and a constraint index of about 1 to 12.

* * * * *